(12) United States Patent
Thomson

(10) Patent No.: US 8,379,210 B2
(45) Date of Patent: Feb. 19, 2013

(54) OPTICAL CELL

(75) Inventor: Alasdair Iain Thomson, Hull (GB)

(73) Assignee: BP Oil International Limited, Middlesex (GB)

( * ) Notice: Subject to any disclaimer, the term of this patent is extended or adjusted under 35 U.S.C. 154(b) by 192 days.

(21) Appl. No.: 12/452,517

(22) PCT Filed: Jul. 4, 2008

(86) PCT No.: PCT/GB2008/002319
§ 371 (c)(1),
(2), (4) Date: Jan. 6, 2010

(87) PCT Pub. No.: WO2009/007699
PCT Pub. Date: Jan. 15, 2009

(65) Prior Publication Data
US 2010/0128256 A1 May 27, 2010

(30) Foreign Application Priority Data
Jul. 6, 2007 (EP) .................................. 07252720

(51) Int. Cl.
*G01N 21/00* (2006.01)
(52) U.S. Cl. .................. 356/440; 356/432; 356/436
(58) Field of Classification Search .......... 356/432–444
See application file for complete search history.

(56) References Cited

U.S. PATENT DOCUMENTS

| | | | |
|---|---|---|---|
| 4,523,841 A | 6/1985 | Brunsting et al. | |
| 5,414,508 A | 5/1995 | Takahashi et al. | |
| 6,147,351 A * | 11/2000 | Huiku | 250/343 |
| 6,657,718 B1 | 12/2003 | Petersen et al. | |
| 2003/0189711 A1* | 10/2003 | Orr et al. | 356/484 |
| 2005/0077489 A1 | 4/2005 | Knapp et al. | |

FOREIGN PATENT DOCUMENTS

| | | |
|---|---|---|
| DE | 198 48 120 | 5/2000 |
| EP | 1 703 272 | 9/2006 |
| GB | 2 431 014 | 4/2007 |

OTHER PUBLICATIONS

International Search Report for PCT/GB2008/002319, mailed Oct. 21, 2008.
Written Opinion of the International Searching Authority for PCT/GB2008/002319, mailed Oct. 21, 2008.

* cited by examiner

*Primary Examiner* — Michael P Stafira
(74) *Attorney, Agent, or Firm* — Nixon & Vanderhye

(57) ABSTRACT

Method of optically analysing a sample by directing one or more frequencies of electromagnetic radiation (EMR) through a sample and onto a partially reflective surface that allows EMR directed thereon to be both reflected and transmitted. The reflected EMR is directed back through the sample such that the pathlength through the sample is different for the transmitted EMR and reflected EMR. The transmitted EMR and reflected EMP are both detected by one or more detectors. The optical absorbance of the sample at the one or more wavelengths of EMR is calculated from the difference between the transmitted EMR and reflected EMR.

9 Claims, 1 Drawing Sheet

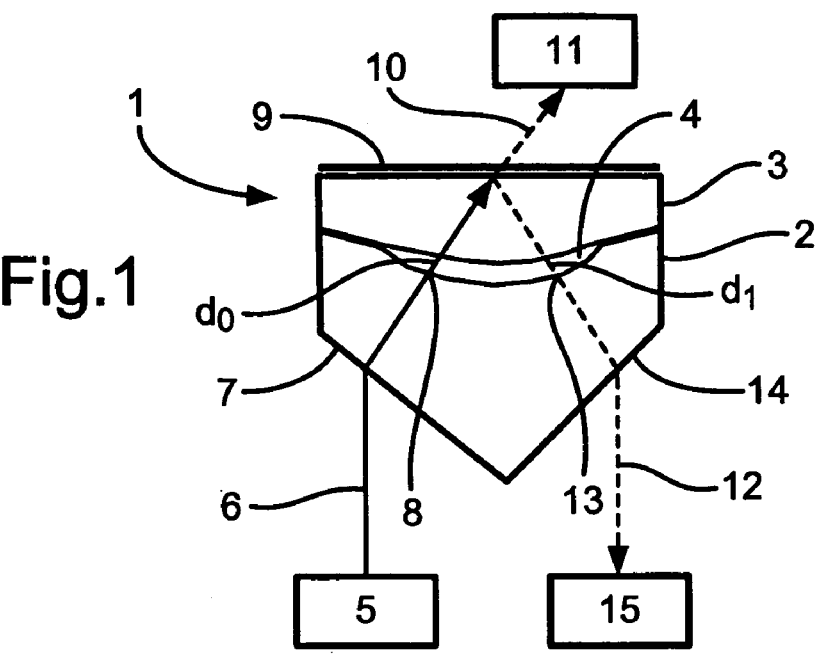
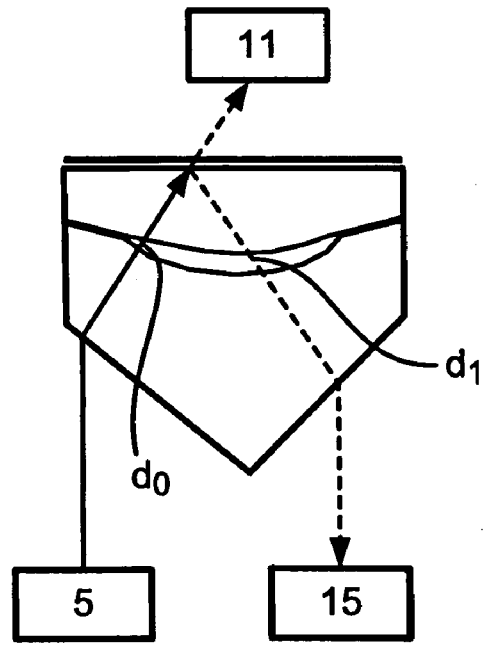

OPTICAL CELL

This application is the U.S. national phase of International Application No. PCT/GB2008/002319, filed 4 Jul. 2008, which designated the U.S. and claims priority to European Application No. 07252720.3, filed 6 Jul. 2007, the entire contents of each of which are hereby incorporated by reference.

This invention relates to the field of optical analysis, more specifically to an apparatus and method for improving background subtraction in optical analysis.

BACKGROUND OF THE INVENTION

When performing optical analysis on a sample, it is desirable to account for background effects, for example the effects of the optical analysis cell and/or the presence of air or components thereof, which may affect the absorption characteristics in the frequency or frequencies of electromagnetic radiation used in the analysis.

In spectroscopic analysis, this can be achieved by first taking a background spectrum in the absence of any sample, followed by a spectrum in which the sample is present, and subtracting the former from the latter. However, the time delay between taking a spectrum of the background and the spectrum of the sample can often be significant. The delay allows the nature of the background to change (for example, a change in moisture composition of the surrounding air), which can reduce the quality of the background subtraction and also introduce noise into the analysis, which negatively impacts the accuracy of the measurements.

In order to resolve temporal effects in the background, dual-beam configurations can be used, in which two beams of electromagnetic radiation are simultaneously directed through separate paths, one containing the sample, and the other without sample. The absorption characteristics of the sample are calculated by subtracting the absorption/reflectance of the sample-free path from the sample-containing path. However, this type of experiment also suffers disadvantages, as the dual-beam equipment can be bulky, and background effects of any optical analysis cell containing the sample to be analysed are not taken into account, and have to be subtracted separately.

In GB 2,431,014, an optical sampling cell is described which has a concave cavity for holding a liquid sample, and in which the cell is made of material transparent to optical radiation. In one embodiment, a reflective surface is used to reflect radiation back through the sample. However, this arrangement does not avoid the need for carrying out a separate background subtraction.

U.S. Pat. No. 6,147,351 describes a method for analysing gas mixtures, in which the gas analysis cell comprises a partially reflective surface that reflects some radiation towards one detector, while allowing transmission of radiation to another detector. This is stated to enable the extent of collision broadening of peaks in a spectrum to be calculated.

DE 19 848 120 describes an arrangement in which a sample cell comprises two partially transmitting mirrors at either end, which causes some of the incident EMR to pass back and forth through the sample until being transmitted and detected. This is stated effectively to increase the sample pathlength, which improves sensitivity, while avoiding complex mirror and optical window arrangements. Additionally, U.S. Pat. No. 5,414,508, a cell is described having partially reflective surfaces on two sides of a sample channel, which improves detection of dilute species. However, the need for a separate background subtraction on the same apparatus in the absence of a sample is still required.

Therefore, there remains a need for improved apparatus and methods for obtaining an optical spectrum of a sample without the need to carry out separate background subtraction.

SUMMARY OF THE INVENTION

According to the present invention, there is provided a method of optically analysing a sample, which method comprises directing one or more frequencies of electromagnetic radiation (EMR) through a sample and onto a partially reflective surface that allows EMR directed thereon to be both reflected and transmitted, which reflected EMR is directed back through the sample such that the pathlength through the sample is different for the transmitted EMR and reflected EMR, which transmitted EMR and reflected EMR are both detected by one or more detectors, characterised in that the optical absorbance of the sample at the one or more wavelengths of EMR is calculated from the difference between the transmitted EMR and reflected EMR.

The present invention enables an optical spectrum of a sample to be obtained without the need to use two separate beams of electromagnetic radiation (EMR), or to perform separate sample-free background measurements. Thus, the apparatus and method of the present invention allows a reduction in the time taken for analysis, and requires simpler and less complex apparatus compared to a dual beam apparatus. A further advantage is that, for experiments conducted at temperatures above or below ambient, the background effects are automatically taken into account by taking the difference between the transmitted and reflected EMR, resulting in improved quality sample spectra being obtainable by reducing the effects of temperature drifts, for example. In addition, by enabling analysis to be carried out more quickly, the effects of noise resulting from temporal changes in the background are reduced.

In the present invention, an optical cell can be used which allows electromagnetic radiation (EMR) that is directed therein to pass through a sample to be analysed, before reaching the partially reflective surface. The partially reflective surface is capable of both reflecting and transmitting the incident EMR directed thereon, the reflected EMR passing back through the sample and out of the optical cell. The optical cell can advantageously be used in conjunction with two EMR detectors, such that both the transmitted and reflected EMR can be separately detected either simultaneously or in quick succession.

The optical cell is made from or comprises a material that is at least partially transparent to the EMR used for the analysis. Quartz or fused silica are generally suitable for UV/Visible and NIR applications, while additional materials suitable for use in NIR measurements include borosilicate glass and sapphire. Materials such as NaCl or CsI can be used for MIR applications. In one embodiment, the entire body of the optical cell is made from EMR-transparent material. In an alternative embodiment, the optical cell comprises windows which allow passage of incident, reflected and transmitted EMR into and out of the optical cell.

The difference between the transmission and reflectance measurements is that the reflected radiation passes through the sample twice, and hence has a longer sample pathlength compared to the transmitted radiation. As the absorption by the sample is typically significantly greater than that of the background, then the sample-related absorbance can be distinguished from the background by comparing the increased sample-related absorbances of the reflected EMR measurements with the corresponding transmitted EMR measurements. As the background associated with the reflected and transmission EMR is the same or similar, then taking the difference between the transmitted EMR and reflected EMR measurements provides the optical absorbance characteristics of the sample.

In one embodiment of the invention, the optical cell comprises a sample area or cavity. To enable sample to be placed within the sample cavity, the optical cell can be formed of two separable pieces which, when fitted together, form the space or cavity in which the sample is held. The partially reflective surface of the optical cell is typically on the opposite side of the sample to where incident EMR is directed. In order to ensure that incident EMR passes through the sample and onto the partially reflective surface, the optical cell can be shaped to ensure that the incident EMR is refracted at a suitable angle. In one embodiment, the partially reflective surface can be on a surface of the sample area or cavity, while in another embodiment it may be on an external surface of the optical cell.

In one embodiment, the sample cavity has a crescent-shaped cross section, resulting in regions of higher and lower sample thickness and hence different optical path-length. An advantage of using a crescent-shaped sample cavity is that it can reduce the extent of interference fringes when using a laser EMR source, or a plurality of EMR wavelengths. This is desirable because Etalon fringes have a negative effect on spectral quality, and reduce the efficiency of background subtraction.

The optical cell can form part of a larger optical apparatus, which in one embodiment comprises an EMR source and two EMR detectors, one of which is used to detect transmitted EMR, and the other to detect reflected EMR. The optical cell can be adapted to fit existing photometers or spectrometers, although the materials used to fabricate the optical cell, for example the transparent nature of the body and the reflective nature of the partially reflective surface, will be determined by the nature of the one or more wavelengths of EMR employed in the analysis, which are typically in the mid-infrared (MIR), near infrared (NIR) or UV/Visible regions of the spectrum. In one embodiment, the EMR source is a tunable diode laser.

The partially reflective surface can be a coating of reflective material, for example a metallic film. Almost any metal can be used for NIR or MIR measurements, gold or aluminium being but two examples. Non-coloured metals are more suitably used for UV/Visible applications. In one embodiment of the invention, the transmitting properties of the partially reflective coating result from it being sufficiently thin so that not all the incident EMR is reflected. In an alternative embodiment, the partially reflective coating is non-continuous, such that a portion of the incident EMR does not contact any reflective material. In one embodiment, the partially reflective surface is on one face or surface of the sample cavity, on the opposite side of the sample cavity to where the incident EMR is directed.

The sample pathlength of the reflected EMR through the sample is not the same as that of the incident EMR. For example, where the sample cavity has a cross-section of uniform width, for example a square or rectangular cross-section, then the sample pathlength of the reflected EMR will be twice that of the transmitted EMR. In the case of a sample cavity with a crescent-shaped cross section, for example, the path of incident EMR through the sample can be modified or adapted so that it passes through a thinner or thicker region of sample than the reflected EMR. This can be modified, depending on the nature of the sample and on the EMR wavelength(s) being used, in order to maximise spectral quality and reduce noise. The difference between the transmitted and reflected spectra is therefore based on the increased absorbance associated with the reflected spectrum compared to the transmitted spectrum, and hence by subtracting one spectrum from the other the spectrum of the sample is obtained, and negates the need to carry out a separate background subtraction. However, in an alternative embodiment, the quality of the spectrum efficiency of the background subtraction can if necessary be enhanced by use of multivariate chemometrics analysis techniques, as know in the art.

The present invention is suitable for laser spectroscopy techniques, for example using a tunable diode laser. Laser spectroscopy is generally more accurate and sensitive than non-laser techniques, and can therefore be useful in the detection and quantification of dilute species in a mixture.

Although features of the cell, such as the crescent-shaped sample cavity, can help to reduce the appearance of phenomena such as Etalon interference fringes, which often arise when using laser techniques, they do not necessarily completely eliminate their appearance. Thus, an advantage of the method of the present invention is that undesirable effects often associated with laser spectroscopy, such as the appearance of Etalon fringes or other multiple reflectance, polarisation or modal effects, can also be subtracted from the sample contribution when the difference between the reflected and transmitted EMR spectra is calculated.

According to another aspect of the present invention there is provided a method of optically analysing a sample comprising the steps of;

(a) loading an optical cell with a reference material and directing a plurality of wavelengths of electromagnetic radiation (EMR) therein, which optical cell is made from or comprises an EMR-transparent material that allows incident EMR to pass into the cell, interact with the reference material, and allows reflected and/or transmitted EMR to leave the cell where it is detected by one or more detectors;

(b) calculating the optical properties of the reference material and background from the differences between the incident EMR and the reflected and/or transmitted EMR from step (a), wherein the background includes the optical properties of the optical cell;

(c) calculating the optical properties of the background by removing the contribution of the reference material from the optical properties of the reference material and background calculated in step (b);

which method also comprises the prior or subsequent steps of;

(d) loading the optical cell with the sample, and directing a plurality of wavelengths of electromagnetic radiation (EMR) therein;

(e) calculating the optical properties of the sample and background from the differences between the incident EMR and the reflected and/or transmitted EMR from step (d);

the optical properties of the sample being calculated by subtracting the optical properties of the background calculated in step (c) from the optical properties of the sample and background from step (e), characterised in that the difference in refractive index of the reference material and the EMR-transparent material of the optical cell is less than 10%.

In order to remove, or at least reduce, the interference effects of Etalon fringes that can appear during optical analysis employing two or more frequencies of EMR, for example in spectroscopic analysis, then measurements can be collected for a reference material that has a similar refractive index to the EMR-transparent material of the optical cell at the wavelengths used in the analysis. This prevents, or at least reduces, the etalon interference patterns, which improves the quality of the spectrum so obtained. By removing the contribution of the reference material from the obtained measurements, then a high quality background spectrum incorporating absorption effects of the optical cell and other effects such as absorption by atmospheric components, can be obtained.

To reduce the extent of etalon interference fringes sufficiently, the difference in the refractive indexes of the EMR-transparent material and the reference material is less than 10%, more preferably less than 5%, and even more preferably less than 3%. A suitable parameter for comparing the refractive index is the so-called $\eta_{20}$ value, which is the refractive index at 20° C. for radiation with a wavelength of 589 nm. For an optical cell made from or comprising borosilicate glass, fused silica or quartz for example, then toluene is a suitable reference material as the $\eta_{20}$ for toluene is 1.4961; and the values for silicate or borosilicate glasses typically range from 1.45 to 1.53. As the absorption spectrum of toluene is well known, then the toluene contributions can be subtracted from the so-obtained spectrum to produce a high quality background spectrum. This background spectrum can then be subtracted from the spectrum of any sample collected using the optical cell, resulting in an improved quality background-subtracted sample spectrum. Where such a technique is employed using an optical cell as herein described, such measurements can also be made to confirm the accuracy of the background subtraction determined from the differences between transmitted and reflected measurements.

It is to be noted that there is no necessity for the reference material to be analysed before the sample. Thus, in one embodiment of the invention the sample is analysed first, and the reference material subsequently. Furthermore, it may be possible to perform a single measurement on a reference material, and subtract the background calculated therefrom from a plurality of samples analysed using the same cell.

BRIEF DESCRIPTION OF THE DRAWINGS

There now follows a non-limiting example illustrating the invention, with reference to the Figures in which:

FIG. 1 schematically shows an apparatus having an optical cell in having a partially reflective surface, illustrating the path of reflected and transmitted EMR.

FIG. 2 schematically shows how the optical pathlength of incident and reflected EMR in the optical cell illustrated in FIG. 1 can be varied by altering the relative position of the optical cell relative to the incident EMR source.

FIG. 1 shows an optical cell 1 with two separable parts 2 and 3 which, when combined together, form a cavity with a crescent-shaped cross-section 4 in which a sample is held. An optical apparatus housing the optical cell comprises an NIR radiation source 5, which directs one or more wavelengths of incident EMR 6 into the optical cell through face 7. The incident beam passes through the sample in cavity 4 at point 8 having thickness $d_0$. The beam hits partially reflective surface 9, and results in a transmitted beam 10, which reaches a first detector 11, and a reflected beam 12, which passes back through the sample in cavity 4 at point 13 having thickness $d_1$. In this example, $d_0$ and $d_1$ are the same. The reflected beam continues through a second face 14 of the optical cell, and reaches a second detector 15.

FIG. 2 shows the same apparatus and optical cell arrangements as shown in FIG. 1, except that the relative position of sample cavity 4 and EMR source 5 has been changed. In this case, the incident EMR beam 6 passes through the sample in cavity 4 at a point where $d_0$ is less than $d_1$. The first detector is also positioned differently relative to the optical cell in order to receive the transmitted EMR beam 11. In this example, the variable arrangement is most suitable achieved by maintaining the positions of the EMR source and the two detectors, and allowing the position of the optical cell to be varied.

The invention claimed is:

1. A method of optically analyzing a sample, which method comprises: directing one or more frequencies of electromagnetic radiation (EMR) through a sample in a sample cavity and onto a partially reflective surface that allows EMR directed thereon to be both reflected and transmitted, wherein the partially reflective surface is on one side of the sample cavity, on the opposite side of the cavity to where the incident EMR is directed, directing reflected EMR back through the sample such that the pathlength through the sample is different for the transmitted EMR which passes through the sample once and the reflected EMR which passes through the sample twice, detecting both transmitted EMR and reflected EMR by one or more detectors, wherein the optical absorbance of the sample at the one or more wavelengths of EMR is calculated from the difference between the transmitted EMR and reflected EMR.

2. A method as claimed in claim 1, employing an optical cell made from or comprising materials that are at least partially transparent to the EMR, which optical cell has said sample cavity for holding the sample, and also comprises the partially reflective surface.

3. A method as claimed in claim 2, in which the optical cell is made from borosilicate glass, fused silica or quartz.

4. A method as claimed in claim 1, in which the partially reflective surface is a metallic coating.

5. A method as claimed in claim 4, in which the metallic coating is aluminium or gold.

6. A method as claimed in claim 1, in which the one or more frequencies of EMR radiation are in the mid infrared and/or near infrared region.

7. A method as claimed in claim 1, in which the source of EMR is a laser.

8. A method as claimed in claim 7, in which the source of EMR is a tunable diode laser.

9. A method as claimed in claim 1, in which there are two EMR detectors, one for detecting transmitted EMR, and another for detecting reflected EMR.

* * * * *